United States Patent
Williamson et al.

(10) Patent No.: US 10,426,956 B2
(45) Date of Patent: Oct. 1, 2019

(54) SYSTEM AND METHOD FOR MONITORING AND CONTROLLING NERVOUS SYSTEM BEHAVIOR USING AUTONOMIC FEATURES

(71) Applicant: Unversity of Florida Research Foundation, Inc., Gainesville, FL (US)

(72) Inventors: John Bonar Williamson, Gainesville, FL (US); Damon Geoffrey Lamb, Gainesville, FL (US); Eric S. Carter Porges, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/535,965

(22) PCT Filed: Dec. 14, 2015

(86) PCT No.: PCT/US2015/065524
§ 371 (c)(1),
(2) Date: Jun. 14, 2017

(87) PCT Pub. No.: WO2016/100195
PCT Pub. Date: Jun. 23, 2016

(65) Prior Publication Data
US 2017/0361097 A1    Dec. 21, 2017

Related U.S. Application Data (60) Provisional application No. 62/091,785, filed on Dec. 15, 2014.

(51) Int. Cl.
*A61N 1/36* (2006.01)

(52) U.S. Cl.
CPC ..... *A61N 1/36031* (2017.08); *A61N 1/36014* (2013.01); *A61N 1/36021* (2013.01); *A61N 1/36025* (2013.01)

(58) Field of Classification Search
CPC ............ A61N 1/36031; A61N 1/36025; A61N 1/36014; A61N 1/36021
See application file for complete search history.

(56) References Cited

U.S. PATENT DOCUMENTS

| | | |
|---|---|---|
| 2006/0122675 A1 | 6/2006 | Libbus et al. |
| 2006/0122676 A1 | 6/2006 | Ko et al. |
| 2008/0147138 A1 | 6/2008 | Rom |

(Continued)

FOREIGN PATENT DOCUMENTS

WO    20160100195    6/2016

OTHER PUBLICATIONS

International Search Report dated Apr. 1, 2016 for PCT/US15/065524 filed Dec. 14, 2015.

(Continued)

*Primary Examiner* — Catherine M Voorhees
(74) *Attorney, Agent, or Firm* — Timothy H. Van Dyke; Beusse, Wolter, Sanks & Maire PLLC (57) ABSTRACT

Respiratory sinus arrhythmia, or another bodily function that indicates a patient's parasympathetic tone, is used to control the delivery of vagal nerve stimulation to the patient for treating disorders that can be reflected and influenced by the behavior of the autonomic nervous system.

18 Claims, 8 Drawing Sheets

(56) References Cited

U.S. PATENT DOCUMENTS

| | | | | |
|---|---|---|---|---|
| 2008/0249439 A1* | 10/2008 | Tracey | ............... | A61H 39/04 601/46 |
| 2008/0319513 A1* | 12/2008 | Pu | ............... | A61N 1/36114 607/62 |
| 2009/0234406 A1* | 9/2009 | Shuros | ............... | A61N 1/36114 607/11 |
| 2013/0066395 A1* | 3/2013 | Simon | ............... | A61N 2/006 607/48 |
| 2013/0211471 A1* | 8/2013 | Libbus | ............... | A61N 1/36114 607/18 |
| 2013/0245722 A1* | 9/2013 | Ternes | ............... | A61N 1/36053 607/62 |
| 2014/0358193 A1* | 12/2014 | Lyons | ............... | A61N 1/0484 607/48 |
| 2015/0306395 A1* | 10/2015 | Libbus | ............... | A61N 1/36146 607/60 |

OTHER PUBLICATIONS

Written Opinion dated Apr. 1, 2016 for for PCT/US15/065524 filed Dec. 14, 2015.

* cited by examiner

PRIOR ART
*FIG. 1*

PRIOR ART

SYSTEM AND METHOD FOR MONITORING AND CONTROLLING NERVOUS SYSTEM BEHAVIOR USING AUTONOMIC FEATURES

FIELD OF THE INVENTION

The invention relates to treatment of non-cardiovascular pathologies of the autonomic nervous system of human beings, and more particularly relates to treatment of brain related disorders such as anxiety, depression, post-traumatic stress disorder, sleep disorders, and chronic pain. In its most immediate sense, the invention relates to vagal nerve stimulation.

BACKGROUND OF THE INVENTION

The vagus nerve is the key component of the parasympathetic branch of a human being's autonomic nervous system. The autonomic nervous system regulates many body organs that operate on a largely subconscious level, such as the heart, lungs, eyes, glands, and digestive tract. When the vagal nerve is electrically stimulated ("vagal nerve stimulation") the operation of the autonomic nervous system is affected. Vagal nerve stimulation is FDA approved for treatment of epilepsy and for depression.

When used to treat epilepsy and depression, vagal nerve stimulation is carried out using an "open loop" protocol; a predetermined degree of stimulation is applied for a predetermined period of time, without regard for the affect that the stimulation is actually having on the patient. As a result, patients can be over-stimulated, causing side effects (examples include, but are not limited to hoarseness of breath, sleep apnea, etc.) that some patients consider to be intolerable. These side effects also preclude use of this technology with other conditions that may otherwise benefit from its use as a first line treatment (e.g., chronic pain, sleep disorders).

It has also been proposed to use a "closed-loop" vagal nerve stimulation protocol to treat cardiovascular issues. For example, patent application publication US 2006/0122676 A1 discloses a device in which vagal nerve stimulation is used to protect the myocardium from further remodeling and predisposition to fatal arrhythmias after the patient has had a heart attack. Some embodiments of the device regulate the vagal nerve stimulation in accordance with the patient's response thereto, such response being determined by measuring the patient's ECG, blood pressure, heart rate, "and the like", and some embodiments allow the patient to initiate the vagal nerve stimulation.

Certain non-cardiovascular diseases, such as anxiety, depression, post-traumatic stress disorder, inflammatory disorders, sleep disorders and chronic pain involve the autonomic nervous system. And, further, behavior of the autonomic nervous system can reflect the behavior of core brain systems involved in these disorders. In other words, autonomic nervous system attributes can be used as an indicator of brain behavior such that more complicated and dangerous solutions (e.g., direct cortical monitoring) are unnecessary to close the loop. It would be advantageous to be able to treat such non-cardiovascular diseases using a closed-loop vagal nerve stimulation protocol to avoid applying excessive stimulation and thereby avoid the side effects that such excessive stimulation can create whilst maximizing the effectiveness/timing of said stimulation with regards to individualized patient profiles/responses.

SUMMARY OF THE INVENTION

The invention proceeds from the realization that such a closed-loop protocol can be achieved by monitoring an index of the patient's parasympathetic nervous behavior (such as respiratory sinus arrhythmia or respiratory hippus variability) and using the effect of the vagal nerve stimulation on the monitored index to determine whether vagal nerve stimulation should be initiated or discontinued, and what the parameters of vagal nerve stimulation (e.g., frequency, amplitude, duration, wave form) should be. This is because the monitored index is representative of the patient's parasympathetic tone, which in turn represents the state of the parasympathetic branch of the patient's autonomic nervous system. (It will be understood that parasympathetic tone cannot be measured directly at present, but can be inferred based upon bodily functions such as respiratory sinus arrhythmia and hippus variability.) This parasympathetic tone can be considered an index of top-down or brain related active influence on the mobilization of autonomic resources to perform various essential tasks.

Accordingly, apparatus in accordance with the invention includes monitoring means for continuously monitoring an index of the patient's parasympathetic nervous behavior, stimulating means for stimulating the autonomic nervous system, and controlling means operatively connected to the monitoring means and to the stimulating means, the controlling means continuously regulating the stimulating means in a manner that said autonomic nervous system is stimulated in accordance with the monitored index of the patient. This permits vagal nerve stimulation to be delivered using a closed-loop protocol to treat non-cardiovascular diseases such as anxiety, depression, post-traumatic stress disorder, inflammatory disorders, sleep disorders and chronic pain.

In preferred embodiments, the monitoring means also monitors the heart rate and estimates parasympathetic influences on the heart rate of the patient and the stimulating means stimulates the vagus nerve, or other cranial nerve with input into autonomic/limbic networks including but not limited to the nucleus accumbens, nucleus of the solitary tract, and nucleus ambiguus.

In preferred embodiments, means for suspending stimulation of the autonomic nervous system is also provided. This can be manually operated by the patient, automatically operated by patient activity that exceeds predetermined threshold intensity, or automatically operated by passage of time.

A method of treating a non-cardiovascular disorder that is reflected and influenced by the autonomic nervous system in a human patient in accordance with the invention comprises the steps of: monitoring a bodily function that represents the patient's parasympathetic tone (or, co-occurring sympathetic process [e.g., skin conductance]); determining, based upon said monitoring of said bodily function, whether stimulation of said autonomic nervous system is indicated or otherwise desired; if stimulation of said autonomic nervous system is desired, stimulating said autonomic nervous system; continuing to monitor said bodily function; and controlling stimulation of said autonomic nervous system in accordance with said bodily function. Advantageously, and in accordance with a preferred embodiment of the inventive method, the bodily function is respiratory sinus arrhythmia, but it can alternatively be another autonomic measure that either co-occurs with alterations in respiratory sinus arrhythmia or is indirectly modifiable by changes in parasympathetic activity such that there is a definable and mechanistically relevant shift (e.g., changes in sympathetic measures such as skin conductance or pre-ejection pulse period; other heart rate variability derived measures including relationships between high, low and very low frequency activity).

BRIEF DESCRIPTION OF THE DRAWINGS

A more complete understanding of the present invention, and the attendant advantages and features thereof, will be more readily understood by reference to the following detailed description when considered in conjunction with the accompanying non-limiting drawings wherein.

DETAILED DESCRIPTION OF PREFERRED EMBODIMENTS

As required, embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

The drawings are not to scale. Each individual element is always indicated by the same reference numeral or legend in all the Figures. Corresponding elements are indicated with primed reference numerals.

Figure 1:
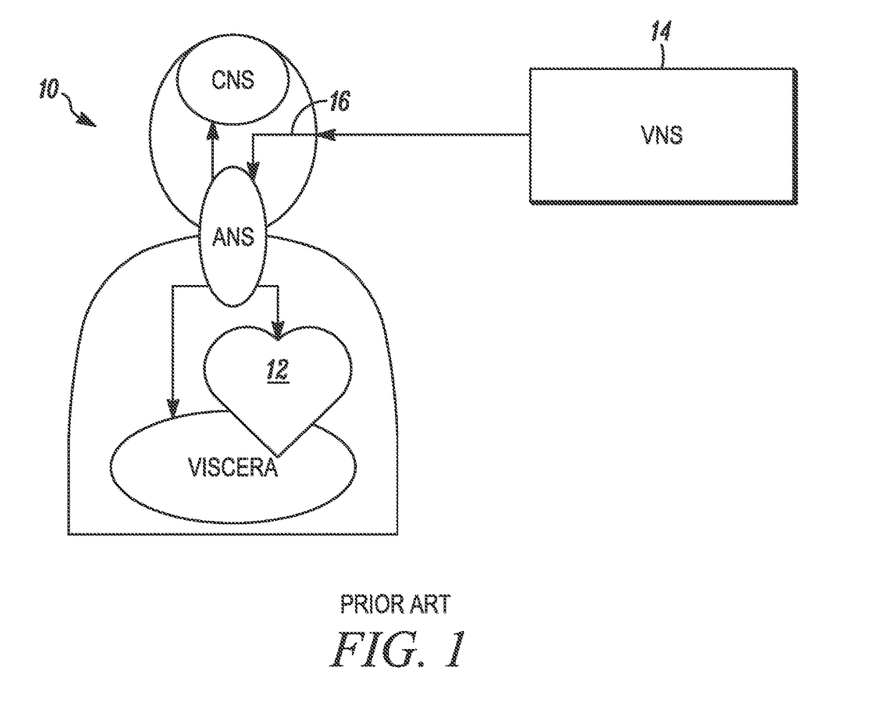
FIG. 1 is a diagram that schematically illustrates a prior art vagal nerve stimulation system that is external to the patient.
Figure 2:
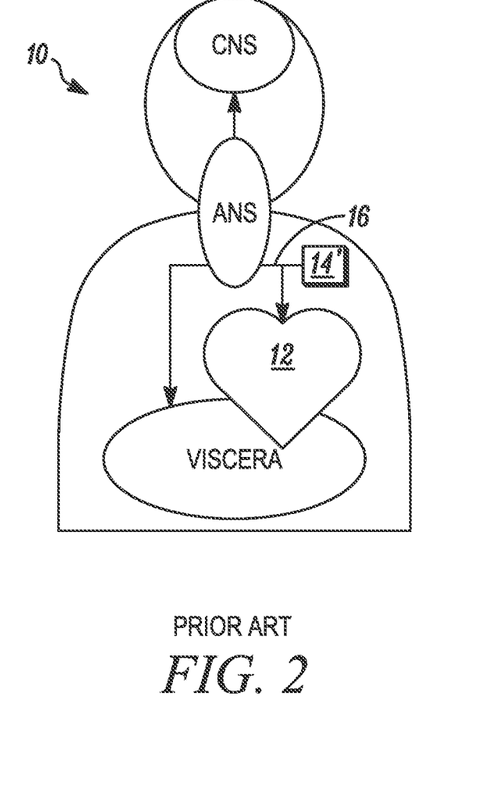
FIG. 2 is a diagram that schematically illustrates a prior art vagal nerve stimulation system that is embedded within the patient.

In FIG. 1, a patient generally indicated by reference numeral 10 has viscera, a central nervous system CNS, an autonomic nervous system (ANS), and a heart 12. A vagal nerve stimulator 14 that is external to the patient 10 delivers electrical stimulation to the autonomic nervous system ANS via a nerve 16, which may be the vagus nerve or other cranial nerves that have input into autonomic/limbic systems including the nucleus ambiguous, nucleus accumbens, and nucleus of the solitary tract. FIG. 2 is similar, except that the vagal nerve stimulator 14' is internal to the patient 10. The vagal nerve stimulator 14' delivers electrical stimulation to the autonomic nervous system ANS via the nerve 16, which as was the case for FIG. 1, can be the vagus nerve or another cranial nerve as previously specified. While stimulators 14 and 14' are described as delivering electrical stimulation, the present invention contemplates that other types of stimulation, such as radio-frequency, light, vibration, or any other suitable stimulation could be used.

Figure 3:
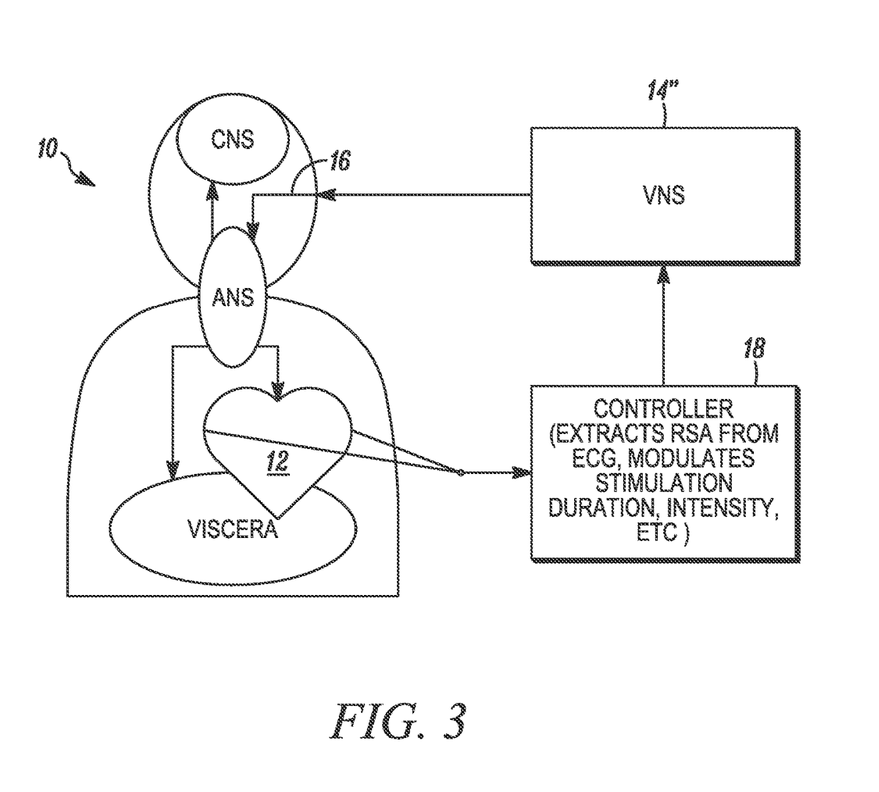
FIG. 3 is a diagram that schematically illustrates a vagal nerve stimulation system in accordance with the invention that is external to the patient.

In a preferred embodiment schematically illustrated in FIG. 3, a controller 18 is operatively connected to the heart 12 of the patient 10. The controller 18, which is external to the patient, extracts the respiratory sinus arrhythmia from the ECG of the heart 12 of the patient 10 and determines (see below) whether vagal nerve stimulation is appropriate for the patient 10 and if so, the appropriate intensity of vagal nerve stimulation required. If vagal nerve stimulation is appropriate, the controller 18 then commands the vagal nerve stimulator 14" to issue appropriately-intense vagal nerve stimulation to the nerve 16 of the patient 10. The vagal nerve stimulator 14" is external to the patient 10. The vagal nerve stimulator 14" and the controller 18 are shown as separate entities, but this is merely for clarity; they may be contained in a common housing.

Figure 4:
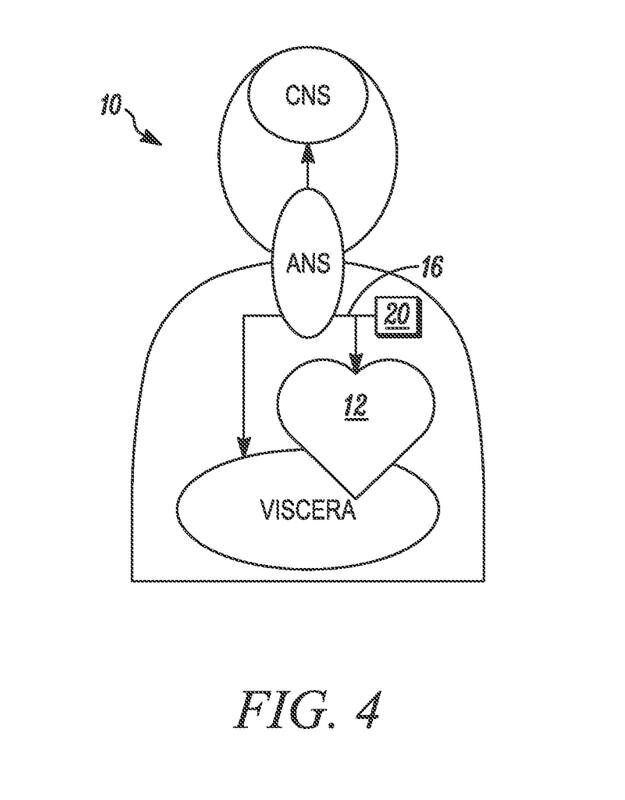
FIG. 4 is a diagram that schematically illustrates a vagal nerve stimulation system in accordance with the invention that is embedded within the patient.

FIG. 4 shows a preferred embodiment of the invention in which a vagal nerve stimulation module is embedded in the patient 10. The vagal nerve stimulation module 20 is functionally identical to the combination of the vagal nerve stimulator 14" and the controller 18; it is shown as a single module, but may in fact be made up of separated components. Vagal nerve stimulation is delivered to the nerve 16.

Non-cardiovascular diseases that can be treated by the system and method according to the invention include, but are not limited to anxiety, depression, post-traumatic stress disorder, inflammatory disorders, sleep disorders, and chronic pain as well as other disorders that involve and/or are reflected by the behavior of the autonomic nervous system. Even if the disease is being treated with another therapy, the system and method according to the invention can be used an adjunct or platform to facilitate response to the other therapy. Non-limited examples include use with medications such as a selective serotonin reuptake inhibitor (SSRI) and use with surgical intervention.

The state of the autonomic nervous system may be represented by physiological signals that reflect parasympathetic, sympathetic tone or a relationship between the two, which cannot be measured directly with standard non-invasive measures but which can be inferred from various bodily functions such as the patient's respiratory sinus arrhythmia or the patient's hippus variability (or other index of parasympathetic nervous behavior) and various measures of skin conductance such as galvanic skin response, galvanic skin level, and skin conductance response. Other bodily functions, such as blood pressure, blood pressure variability, and heart rate, can be used in combination with these bodily functions to represent the patient's parasympathetic tone more accurately.

By using appropriate inputs to the controller 18 and to the vagal nerve stimulation module 20, the stimulation delivered by the vagal nerve stimulator 14" and by the vagal nerve stimulation module 20 can (see below) be appropriately calibrated to the patient 10.

Figure 5:
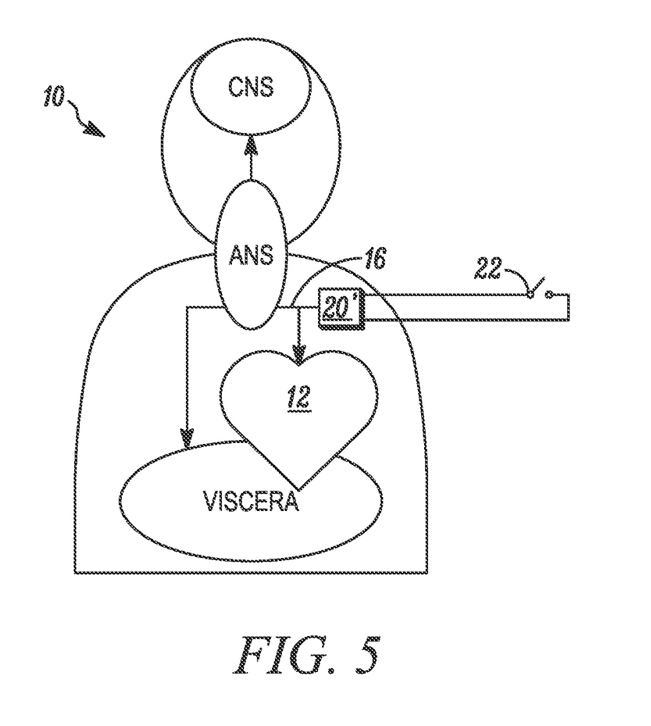
FIG. 5 is a diagram that schematically illustrates a preferred embodiment of a vagal nerve stimulation system in accordance with the invention.

There are circumstances in which a patient such as patient 10 should not be subjected to vagal nerve stimulation or the vagal nerve stimulation should be adjusted to reflect the circumstances. If, for example, the patient 10 is exercising or is about to exercise, the autonomic nervous system should not be stimulated or the stimulation should be adjusted to reflect the exercise. As shown in FIG. 5, a patient-operable means 22 is advantageously provided. The means 22 is operatively connected to the vagal nerve stimulation module 20'. When the patient 10 starts to exercise, begins taking a test, or otherwise engages in an activity during which stimulation of the autonomic nervous system should not occur or should be adjusted to reflect the activity, the patient 10 operates the means 22 to cause stimulation of the autonomic nervous system to be suspended or otherwise altered. The system and method of the present invention may be useful in preventing sudden unexpected death in epilepsy (SUDEP). There is some concern that SUDEP can be exacerbated by conventional VNS, the system and method disclosed herein should have a reduced likelihood because: minimum stimulation is delivered to achieve desired closed loop outcome; and stimulation can be modulated by sleep profile (when SUDEP tends to occur).

Although the means 22 is patient-operable, it is alternatively possible to equip a vagal nerve stimulation module 20" with a means 22' (FIG. 6) for suspending stimulation automatically or adjusted automatically. The means 22' is operatively connected to the vagal nerve stimulation module 20" to stimulation to cease automatically or adjust automatically when the patient's heart rate indicates that the patient has exceeded a predetermined threshold intensity, when stimulation has continued for a predetermined time, when the patient's blood pressure is excessive, or under other circumstances when any stimulation or stimulation at the current parameters (intensity, duration, and/or interval) would be inappropriate.

Figure 7:
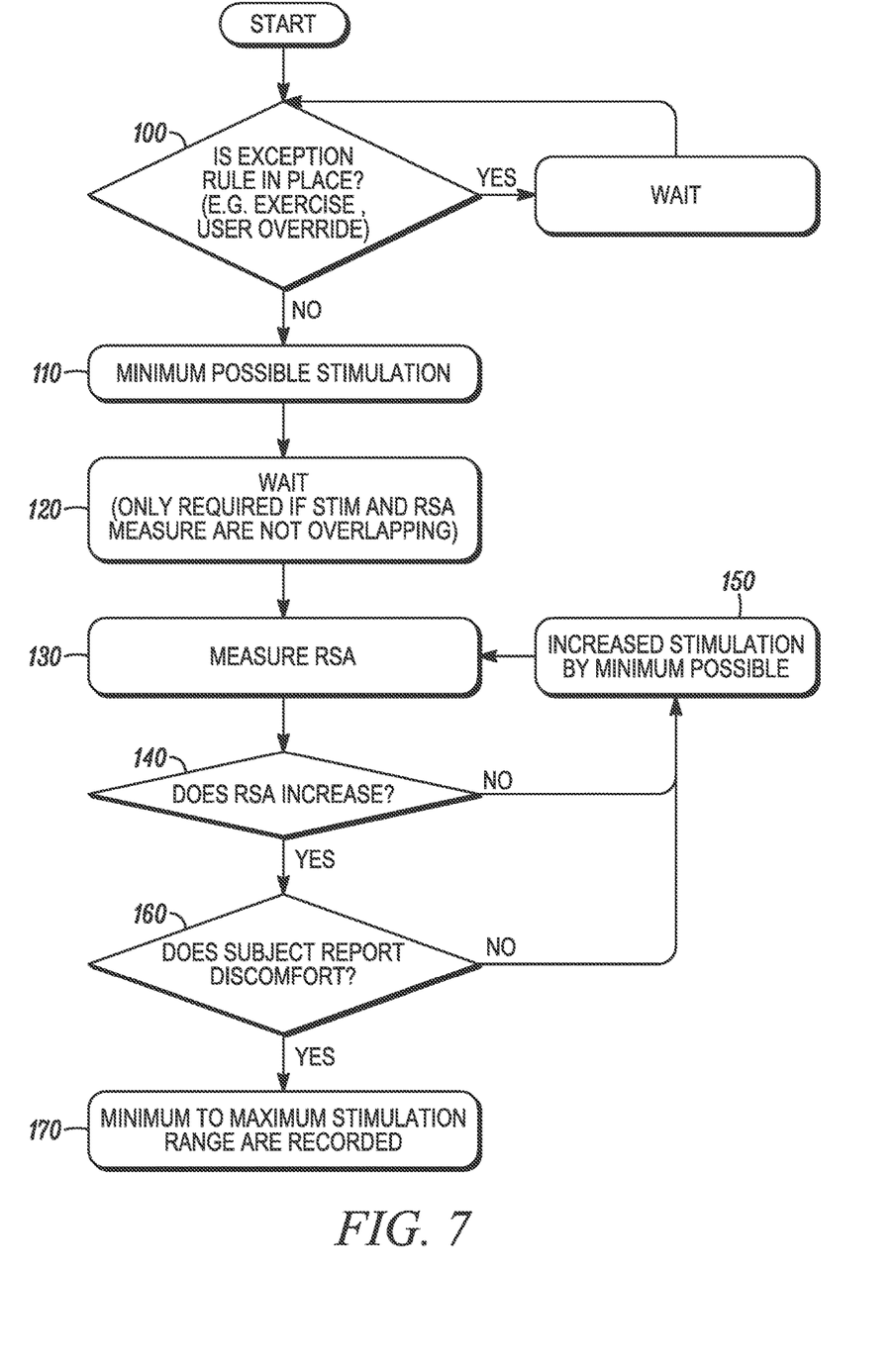
FIG. 7 is a flow chart illustrating how a range of vagal nerve stimulation can be determined for a particular patient.

A patient benefits when the parasympathetic tone of his or her autonomic nervous system is held within an appropriate range for that particular patient. FIG. 7 shows one way in which an appropriate range of vagal nerve stimulation can be determined for a particular patient. Initially, in step 100, it is determined whether the patient has manually caused stimulation of the autonomic nervous system to be suspended or adjusted (as would be the case when the patient is exercising). If so, the determination process is paused until such suspension or manual adjustment has ceased.

Then, in step 110, the minimum vagal nerve stimulation is delivered to the patient. If measurement of the patient's respiratory sinus arrhythmia does not occur while this stimulation is ongoing, the determination process is paused during step 120 until the stimulation has ceased. Then, in step 130, the patient's respiratory sinus arrhythmia is measured. If it is determined in step 140 that the respiratory sinus arrhythmia has not increased, then in step 150 the intensity of the vagal nerve stimulation is incremented. (This incrementation can be accomplished by varying the shape of the stimulating waveform, the amplitude of the stimulation, and the frequency of the stimulation). This process continues until the patient's respiratory sinus arrhythmia increases. At that point, in step 160, it is determined whether the patient reports discomfort from the stimulation. If not, this process is continued with progressive incrementing of the intensity of the vagal nerve stimulation.

But, if in step 160 the patient reports that the vagal nerve stimulation has caused discomfort, this incrementing ceases. The range of vagal nerve stimulation that is appropriate for the patient is defined in step 170 by the minimum stimulation intensity needed to raise the patient's respiratory sinus arrhythmia and the maximum stimulation intensity that does not cause patient discomfort.

Figure 6:
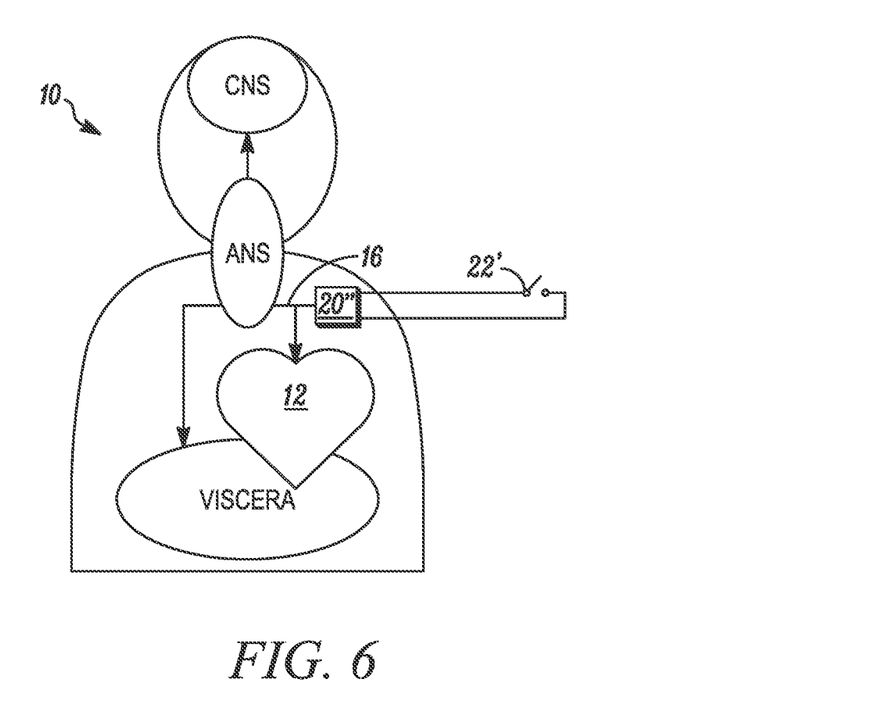
FIG. 6 is a diagram that schematically illustrates another preferred embodiment of a vagal nerve stimulation system in accordance with the invention.
Figure 8:
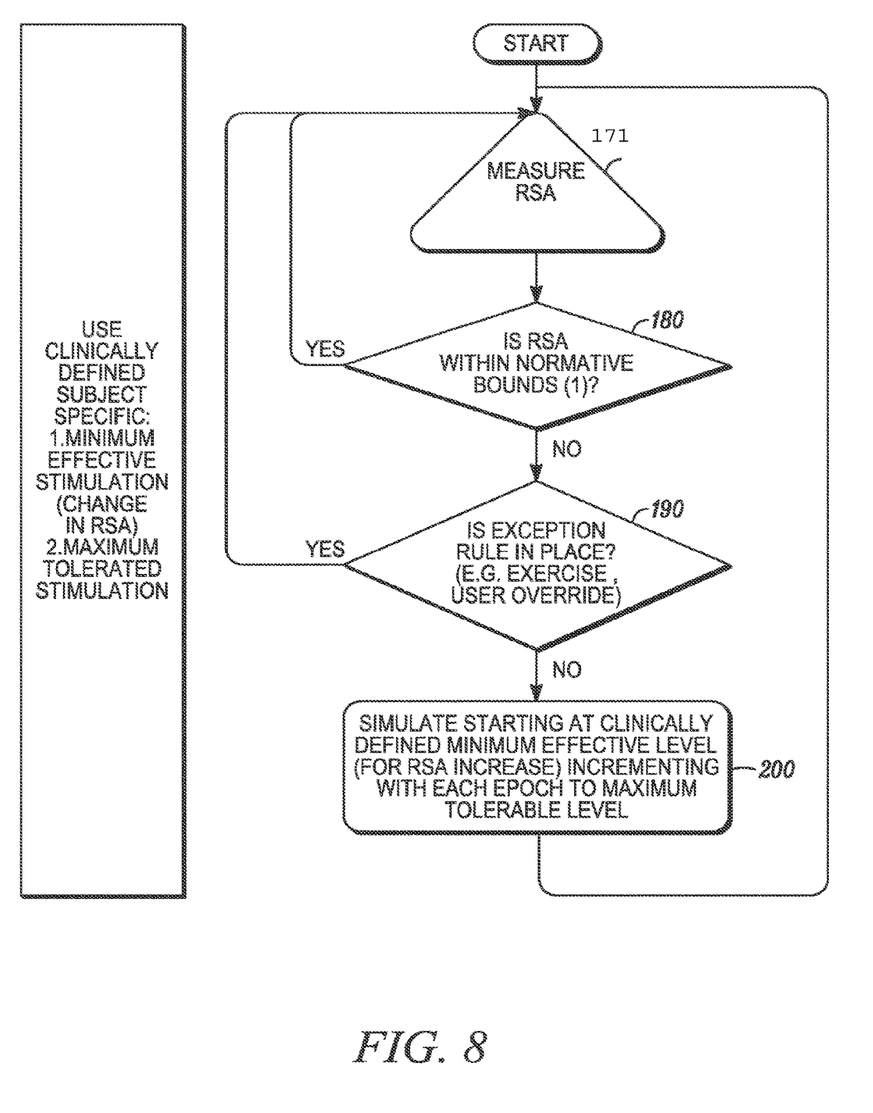
FIG. 8 is a flow chart illustrating operation of a preferred embodiment of the invention.

In FIG. 8, treatment of a patient for a non-cardiovascular disorder involving the autonomic nervous system begins in step 171 with measurement of the patient's respiratory sinus arrhythmia. If, in step 180 this measurement is within that patient's normal range, measurement continues. If not, it is determined in step 190 whether vagal nerve stimulation has been suspended because of e.g. the patient's exercise. If so, measurement continues. But, if not, vagal nerve stimulation commences in step 200 at the minimum intensity determined using the process shown in FIG. 6. The stimulation continues with incremental increases in intensity until the maximum intensity determined using the process shown in FIG. 6 is reached (or until the measured respiratory sinus arrhythmia is within the patient's therapeutic range).

All references cited herein are expressly incorporated by reference in their entirety. It will be appreciated by persons skilled in the art that the present invention is not limited to what has been particularly shown and described herein above. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the invention set forth herein that are within the scope and spirit of the present invention are to be included as further embodiments of the present invention.

What is claimed is:

1. A system for stimulating the central nervous system via a peripheral nerve input into the autonomic nervous system of a human patient in accordance with the state of the parasympathetic branch of the autonomic nervous system, comprising:
   monitoring means for continuously monitoring an index of parasympathetic nervous system behavior of the patient;
   stimulating means for stimulating the autonomic nervous system, wherein the stimulating means stimulates the vagus nerve or trigeminal nerve so that the central nervous system is affected; and
   controlling means operatively connected to the monitoring means and to the stimulating means, the controlling means continuously regulating the stimulating means in a manner that said autonomic nervous system is stimulated in accordance with the monitored index of parasympathetic nervous system behavior of the patient,
   wherein the monitored index comprises respiratory sinus arrhythmia, and, optionally, further comprises hippus variability, skin conductance, blood pressure, blood pressure variability or heart rate, and
   wherein the controlling means regulates the stimulating means to provide minimal stimulation intensity to increase the monitored index via effects on the central nervous system while not causing patient discomfort.

2. The system of claim 1, wherein the stimulating means stimulates the vagus nerve.

3. The system of claim 1, wherein the stimulating means stimulates the trigeminal nerve.

4. The system of claim 1, wherein the monitored index comprises respiratory hippus variability.

5. The system of claim 1, further including means for suspending stimulation of the autonomic nervous system.

6. The system of claim 5, said suspending means being manually operated by the patient.

7. The system of claim 5, said suspending means being automatically operated by patient activity that exceeds a predetermined or dynamically determined threshold intensity.

8. The system of claim 5, said suspending means being automatically operated by passage of time.

9. A method of controlled stimulation of the central nervous system in a human patient, comprising:
monitoring an index of parasympathetic, sympathetic, or derived index of autonomic nervous system behavior of the patient, wherein the monitored index comprises respiratory sinus arrhythmia, and, optionally, further comprises hippus variability, skin conductance, blood pressure, blood pressure variability or heart rate;
determining, based upon said monitoring, whether stimulation of said autonomic nervous system is required;
when stimulation of said autonomic nervous system is required, stimulating said autonomic nervous system as required by said determining step, wherein stimulating said autonomic nervous system comprises stimulating the vagus or trigeminal nerves so that the central nervous system is affected;
continuing to monitor the index of parasympathetic nervous system behavior of the patient; and
controlling stimulation of said autonomic nervous system in accordance with an index of parasympathetic nervous system behavior of the patient,
wherein stimulating comprises providing minimal stimulation intensity to the central nervous system through the autonomic nervous system to thereby increase the monitored index while not causing patient discomfort.

10. The method of claim 9, wherein said controlling step comprises: adjusting intensity of the stimulation; and turning the stimulation on and off.

11. The method of claim 10, wherein the adjusting step is carried out by varying at least one of: stimulation waveform shape; stimulation amplitude; and stimulation frequency.

12. The method of claim 9, wherein said stimulating step comprises the step of stimulating the patient's vagus nerve.

13. The method of claim 9, wherein said stimulating step comprises the step of stimulating the patient's trigeminal nerve.

14. The method of claim 9, wherein said controlling step further comprises terminating stimulation of said autonomic nervous system when the physical activity of the patient exceeds a predetermined threshold.

15. A method of stimulating the autonomic nervous system in a human to affect anxiety, depression, post-traumatic stress disorder or chronic pain in the human, comprising:
monitoring a bodily function, wherein the bodily function comprises respiratory sinus arrhythmia, and, optionally, further comprises hippus variability, skin conductance, blood pressure, blood pressure variability or heart rate;
determining, based upon said monitoring of said bodily function, whether stimulation of said autonomic nervous system is required; if stimulation of said autonomic nervous system is required, stimulating said autonomic nervous system as required by said determining step so that the central nervous system if affected;
continuing to monitor said bodily function; and
controlling stimulation of said autonomic nervous system in accordance with said bodily function, wherein controlling stimulation comprises providing minimal stimulation intensity to increase the bodily function while not causing patient discomfort, wherein stimulating the autonomic nervous system stimulates the central nervous system so as to affect anxiety, depression, post-traumatic stress disorder or chronic pain in the human patient.

16. The method of claim 15, wherein the bodily function comprises a measure of heart rate variability.

17. The method of claim 15, wherein the bodily function comprises a measure of skin conductance.

18. The method of claim 15, wherein the bodily function comprises respiratory hippus variability.

* * * * *